US006716683B1

(12) United States Patent
Bruce et al.

(10) Patent No.: US 6,716,683 B1
(45) Date of Patent: Apr. 6, 2004

(54) OPTICAL ANALYSIS FOR SOI INTEGRATED CIRCUITS

(75) Inventors: Michael R. Bruce, Austin, TX (US); Glen P. Gilfeather, De Valle, TX (US); Rama R. Goruganthu, Austin, TX (US); Jiann Min Chin, Singapore (SG); Shawn McBride, Austin, TX (US)

(73) Assignee: Advanced Mircor Devices, Inc., Sunnyvale, CA (US)

( * ) Notice: Subject to any disclaimer, the term of this patent is extended or adjusted under 35 U.S.C. 154(b) by 161 days.

(21) Appl. No.: 09/887,638

(22) Filed: Jun. 22, 2001

(51) Int. Cl.[7] .......................... H01L 21/00; H01L 21/84
(52) U.S. Cl. .......................................... 438/151; 438/14
(58) Field of Search .................. 438/151, 14; 356/338, 356/318, 344, 237.4; 348/126; 382/149, 312

(56) References Cited

U.S. PATENT DOCUMENTS

| | | | | |
|---|---|---|---|---|
| 4,755,874 A | * | 7/1988 | Esrig et al. ................. 348/126 |
| 5,061,850 A | * | 10/1991 | Kelly et al. ................. 250/306 |
| 5,301,006 A | * | 4/1994 | Bruce ......................... 356/311 |
| 5,391,885 A | * | 2/1995 | Imataki et al. ............ 250/492.2 |
| 5,661,520 A | * | 8/1997 | Bruce ......................... 348/92 |
| 5,754,291 A | * | 5/1998 | Kain .......................... 356/338 |
| 5,940,545 A | | 8/1999 | Kash et al. |
| 6,020,957 A | * | 2/2000 | Rosengaus et al. ........ 356/237.4 |
| 6,031,985 A | * | 2/2000 | Yoshida ..................... 250/492.2 |
| 6,154,274 A | * | 11/2000 | Davis et al. ................. 356/124 |
| 6,262,423 B1 | * | 7/2001 | Hell et al. ................... 250/458.1 |
| 6,262,430 B1 | * | 7/2001 | Li ............................... 250/492.3 |
| 6,411,377 B1 | * | 6/2002 | Noguchi et al. .......... 356/237.4 |
| 6,462,814 B1 | * | 10/2002 | Lo ............................. 356/237.2 |

OTHER PUBLICATIONS

Inoué, Shinya, Video Microscopy, Plenum, 1986, pp. 126–127, 130–131.*

* cited by examiner

*Primary Examiner*—Richard Elms
*Assistant Examiner*—Michael Luhrs

(57) ABSTRACT

An integrated circuit die having silicon on insulator (SOI) structure is analyzed in a manner that enhances the ability to detect photoemissions from the die. According to an example embodiment of the present invention, one of two or more lenses having a higher relative photon count is identified and used to analyze a semiconductor die. The die has at least a portion of the insulator of the SOI structure exposed, and photon emissions are detected using each lens via the exposed insulator in response to the die being stimulated. The number of photons detected using each lens is compared, and the lens having a higher photon count rate is identified, optimizing the photon count for the particular type of die preparation used to expose the insulator. The identified lens is then used with the high-speed detector to detect photoemissions from the die, and the detected photoemissions are used to analyze the die.

30 Claims, 3 Drawing Sheets

OPTICAL ANALYSIS FOR SOI INTEGRATED CIRCUITS

FIELD OF THE INVENTION

The present invention relates generally to semiconductor devices and their fabrication, and more particularly, to techniques for optically analyzing circuitry within an integrated circuit.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors operating at speeds of hundreds of millions of instructions per second to be packaged in relatively small, air-cooled semiconductor device packages.

As manufacturing processes for semiconductor devices and integrated circuits increase in difficulty, methods for testing and debugging these devices become increasingly important. Not only is it important to ensure that individual chips are functional, it is also important to ensure that batches of chips perform consistently. In addition, the ability to detect a defective manufacturing process early is helpful for reducing the number of defective devices manufactured.

One semiconductor analysis method involves optically analyzing integrated circuits in silicon using, for example, microscope-based analysis, picosecond imaging circuit analysis (PICA), and electro-optic probing. Optical analysis of integrated circuits having silicon on insulator (SOI) structure, however, has been challenging. In particular, it has been difficult to detect photoemissions in the visible light range (e.g., visible to near infrared (nIR), or between about 500 nanometers and 1.5 microns) through the insulator of the SOI structure. In addition, die surface preparations used prior to analyzing SOI circuit structure can vary, and the variance affects the ability to optically analyze the circuitry.

SUMMARY OF THE INVENTION

The present invention is directed to approaches for addressing challenges discussed above, including challenges to optical analysis of semiconductor dies having SOI structure, as exemplified in a number of implementations and applications, some example aspects of which are summarized below.

According to an example embodiment of the present invention, an integrated circuit die having silicon on insulator (SOI) structure is analyzed using lens optimization for the detection of photons from the die. An integrated circuit die having at least a portion of the insulator of the SOI structure exposed is stimulated. Visible photon emissions (photoemissions) from the die are detected through the insulator of the SOI with first and second different lenses. The photoemissions detected using the first and second lenses are compared and the one of the first and second lenses that has a higher photon count rate is identified. The lens having a higher photon count rate is then used to detect photoemissions from the die, and the detected photoemissions are used in the analysis of the die. In this manner, optical analysis including photon detection from dies having SOI structure is achieved, and the lens used for the optical analysis is adapted for the particular die preparation used.

In a more particular example embodiment of the present invention, two lenses are used to analyze the die. A photoemission detection lens is identified using the above method, and a second lens is selected for imaging the die with high resolution. The second lens is used to identify a circuit element in the die for analysis, and the first lens is then used to detect photoemissions from the identified circuit element. In this manner, the photoemission detection lens can be optimized for detection of photons, and the circuit identification lens can be optimized for imaging the die. In one implementation, the two-lens analysis is accomplished in a single detection arrangement adapted to use both lenses.

In another example embodiment of the present invention, a system is adapted for the detection of photons from an integrated circuit die having SOI structure. The system includes a substrate removal arrangement adapted to provide an integrated circuit die having at least a portion of the insulator of the SOI structure exposed. A die analysis tool is adapted to stimulate the integrated circuit die in a manner that generates photoemissions. A detector is used to detect the photoemissions from the die via the insulator of the SOI structure with a first lens and another detector is used to detect photon emissions from the die via the insulator with a second lens that is different from the first lens. A comparison arrangement is adapted to compare the photon emissions detected using the first and second lenses and to identify which of the first and second lenses has a higher photon count rate. Once the lens having the higher photon count rate is identified, a detector is adapted to use the identified lens to detect photoemissions from the die, and the detected photoemissions are used for analyzing the die.

The above summary is not intended to describe each illustrated embodiment or every implementation. The figures and detailed description that follow more particularly exemplify these embodiments.

BRIEF DESCRIPTION OF THE DRAWINGS

The present invention may be more completely understood in consideration of the following detailed description of various embodiments in connection with the accompanying drawings, in which.

Figure 1:
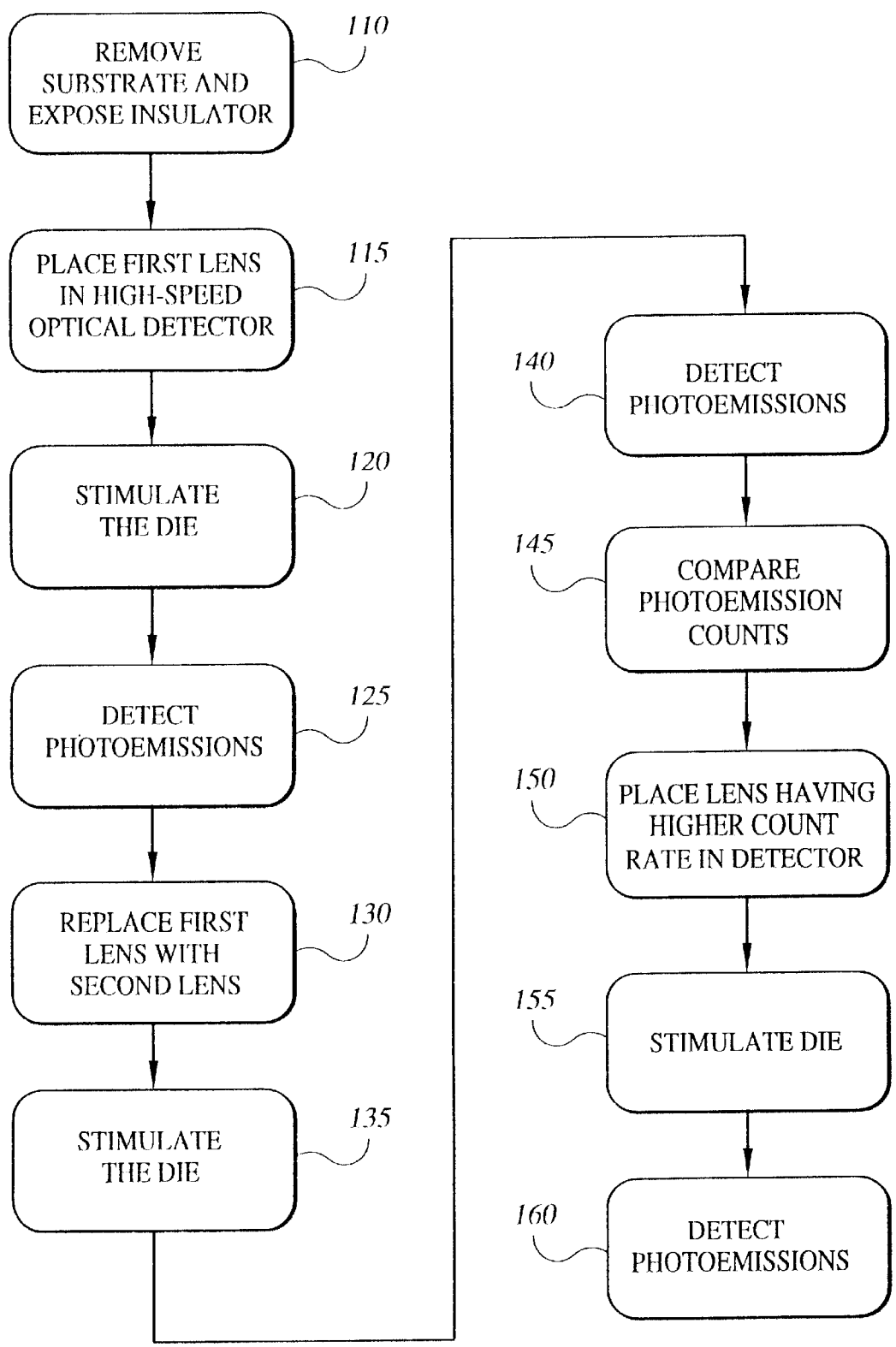
FIG. 1 is a flow diagram for analyzing an integrated circuit die, according to an example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

Implementations of the present invention are believed to be applicable for a variety of different types of semiconductor devices, and have been found particularly suited to optical analysis of integrated circuits having silicon on insulator (SOI) structure. While not necessarily limited to such devices, various aspects may be appreciated through a discussion of examples using this context.

In connection with an example embodiment of the present invention, it has been discovered that the detection of visible photons from an integrated circuit die having SOI structure using a high-speed optical detector is made possible via an appropriate lens-optimization approach, and that the visible photons can be used for analyzing the die. In one implementation, a first lens is used in the high-speed optical detector to detect photoemissions from an integrated circuit die while the die is undergoing stimulation. The number of photoemissions, or photon counts, detected using the first lens during the stimulation is recorded. The first lens is replaced with a second lens, the die is similarly stimulated and photoemissions from the die are again detected and recorded.

The number of photoemission counts detected via the second lens is compared to the number of counts detected using the first lens. The lens exhibiting a higher count is used in the high-speed optical detector, the die is stimulated again and photoemissions from the die are detected. The detected photoemissions are used to detect a characteristic of the die related to the photoemissions, such as temperature, electronic activity, the timing of a state-changing operation or a state of a selected circuit element.

In one specific implementation, it has been unexpectedly discovered that a lens having a numerical aperture (NA) of about 0.75 NA has a higher efficiency for gathering photoemissions as compared to a lens having a 0.85 NA. This is counter-intuitive because the collection efficiency of a lens generally increases as the square of the NA of the lens, which would indicate that the lens having the 0.85 NA should have a higher efficiency than the lens having a 0.75 NA.

FIG. 1 is a flow diagram for a method for analyzing an integrated circuit die having SOI structure, according to a more particular example embodiment of the present invention. At block 110, bulk silicon substrate is removed from the back side of a die and the insulator portion (e.g., buried oxide (BOX)) of SOI structure in the die is exposed. In one implementation, a portion of the buried insulator is exposed to allow the transmission light over a range of between about 200 nanometers and 5 microns. For more information regarding the exposure of the insulator portion and regarding general optical analysis, reference may be made to U.S. patent application Ser. No. 09/247,002 (AMDA.272PA/TT2346), filed on Feb. 8, 1999 and entitled "Test Arrangement and Method for a Thinned Flip-chip IC" now U.S. Pat. No. 6,255,124, which is fully incorporated herein by reference.

A first lens adapted to detect a photoemission from the die through the exposed insulator is placed in a high-speed optical detector at block 115. The photoemission may include, for example, infrared (IR) light, visible light and other types of photon emissions. The die is stimulated at block 120, and photoemissions from the die are detected using the first lens in the high-speed optical detector at block 125. In one implementation, the die is powered in a manner that produces a known PICA signal. The count, or number, of photoemissions detected over a selected time period is recorded.

At block 130, the first lens is replaced with a second lens that is different from the first, and the die is again stimulated in a similar manner (e.g., operated under similar conditions) at block 135. Photoemissions from the die are detected with the high-speed optical detector using the second lens at block 140. The count of photoemissions detected over a selected time period with the second lens is detected and compared to the count of photoemissions detected with the first lens at block 145. The lens having the higher count rate (e.g., number of counts during a unit time) is used with the high-speed optical detector at block 150, the die is stimulated at block 155 and photoemissions are detected from the die with the higher count lens at block 160.

The detected photoemissions can be used to analyze the die in a variety of manners, such as for detecting electron movement in the die (e.g., causing photon emissions), detecting whether the circuit element is operating at a particular logic state and/or detecting whether the circuit element undergoes a state change at an appropriate time. For more information regarding time-related analysis, such as for time-resolved detection of a response from the die, reference may be made to U.S. patent application Ser. No. 09/580,716 (AMDA.437PA/TT3723), filed on May 30, 2000 and entitled "Time Resolved Emission Microscopy System" now U.S. Pat. No. 6,469,529, and Ser. No. 09/409,088 (AMDA.313PA/TT3370), filed on Sep. 30, 1999 and entitled "Quadrant Avalanche Photodiode Time-resolved Detection" now U.S. Pat. No. 6,483,327 which are fully incorporated herein by reference.

In one example embodiment of the present invention, each of the first and second lenses include a plurality of lenses, each of the plurality of lenses having particular optical and surface characteristics that result in loss of light due to reflection. The lens having a higher photon count rate is identified as a function of the optical and surface characteristics and the NA of the lens. It has been discovered that, with a first lens having a comparatively higher NA than a second lens, losses due to surface characteristics with the first lens may be significant enough to counter the advantages of the higher NA and, therefore, make the lens having a lower NA better at collecting photons. In this implementation, a lens having a lower NA but exhibiting less loss due to surface characteristics, resulting in a higher photon count rate, is identified and used to analyze a die.

In another example embodiment of the present invention, wherein the photon count varies as a function of the surface preparation of the die, the lens is identified as a function of the exposed insulator. For example, the type of substrate removal used to expose the buried insulator, the presence or absence of anti reflective coatings over the exposed insulator and the amount of insulator that has been removed can all affect the photons emitted. For each of these and other examples, the lens exhibiting a higher photon count rate may be different, depending upon the application. Once the lens is identified for a semiconductor die exhibiting particular surface preparation characteristics, dies prepared in a similar manner are analyzed using the identified lens.

In a more particular example embodiment of the present invention, an imaging lens that is different from the lens used to detect photoemissions is used to obtain an image of the die that includes items such as circuitry or other die structure. The image of the die is used in connection with the detection of photoemissions to analyze the die. In one implementation, an electronic zoom feature is used to match the field of view (FOV) of the two lenses where the imaging lens used is different in magnification from the photoemission detection lens. In another implementation, the imaging lens is matched in magnification to the photoemission detection lens, matching the FOV of each lens.

In one particular example embodiment of the present invention, the image is used for navigating to a selected portion of the die and photoemissions are obtained from the selected portion with the high-speed optical detector. In this instance, the imaging lens is first used with the high-speed optical detector for focusing the detector to the selected portion. Once the navigation is complete, the lens for detecting photoemissions is used in place of the imaging lens and a photoemission is detected from the selected portion.

In another implementation, the image is used to navigate the high-speed optical detector relative to a reference point on the die. Detected photoemissions are then mapped onto a circuit diagram using the reference point on the circuit to locate the source of the photoemissions. In still another implementation, a reference point is used in connection with a detected photoemission to overlay the photoemission onto the obtained image of the die, and the source of the photoemission is mapped to a circuit portion on the image of the die.

In another example embodiment of the present invention, two or more imaging lenses are used to obtain an image of the die via the exposed insulator. In a similar manner to that described hereinabove regarding the selection of a lens that has a higher photon count, the images taken by the two or more imaging lenses are compared and the lens producing the best image is used for analyzing the die. In this manner, the imaging lens is also optimized for the particular type of die and the manner in which the insulator portion of the die has been exposed.

In another more particular example embodiment of the present invention, photoemissions resulting from a state-changing operation of circuitry in the die are detected. State changing operations that are detectable in connection with the present invention include, for example, a transistor changing between an on and an off state, a circuit element going from a first charge to a second charge, a memory element being refreshed and other commonly-used integrated circuit functions. One detectable characteristic of a state changing operation is a movement of electrons that cause emission of light. The emission of light is detected and used to detect that a state changing operation has occurred. The source of the light emission is identified using the detected photoemission in connection with a circuit image or schematic.

Figure 2:
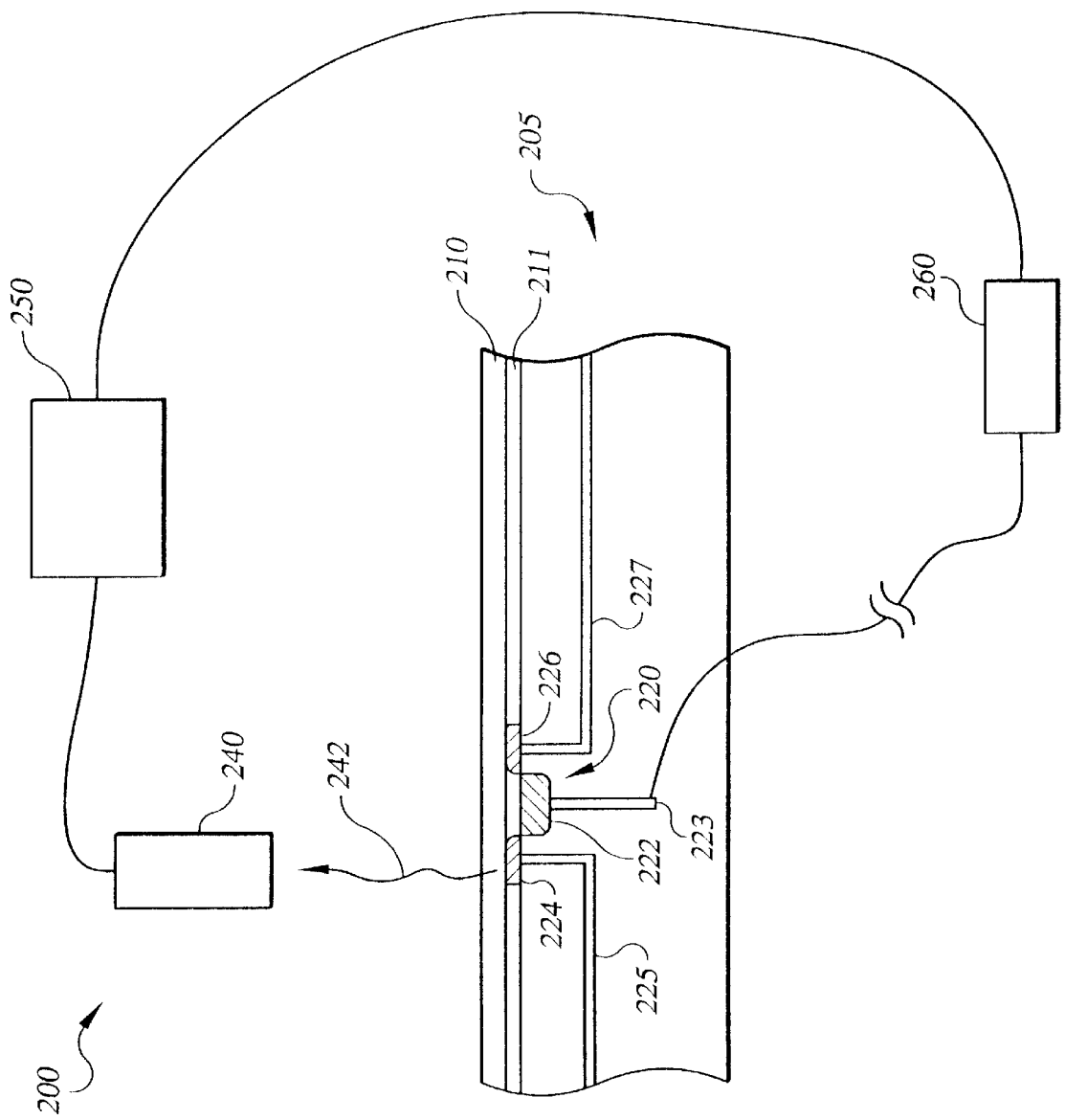
FIG. 2 is a system adapted to analyze an integrated circuit die, according to another example embodiment of the present invention.

FIG. 2 is a system 200 for analyzing a SOI integrated circuit device 205, according to another example embodiment of the present invention. The system includes a high-speed optical detector 240 having interchangeable lenses, each of the lenses having one or more lenses that work together to achieve a selected NA. The system uses a power supply 260 that is electrically coupled to the die and adapted to stimulate the die. In this instance, the device 205 is shown having a transistor 220 formed using SOI structure including a thin layer of silicon 211 formed on an insulator 210. The transistor 220 includes source/drain regions 224 and 226 formed in the thin layer of silicon 211, and a gate 222 formed over the thin layer of silicon. Interconnects 223, 225 and 227 extend from the gate 222 and source/drain regions 224 and 226, respectively. The power supply is coupled via internal circuitry (not shown) via interconnect 223 to gate 222. In response to the stimulation, the die emits a photoemission 242 that is detected by the photon detector 240. The detector is adapted to detect photons via the insulator using two different photon detection lenses and to use the lens having a higher count of detected photons for analyzing the die.

Lenses that may be used in connection with the detector 240 include, for example, a lens having a NA of at least 0.7 NA, a Zeiss 100×0.75 numerical aperture (NA) lens; a Nikon-Hamamatsu 100×0.85NA lens and a Mititoyo 50×0.42 NA nIR lens. In one specific implementation, the lens used includes at least two lenses formed having an interface that eliminates an air-lens interface. In another implementation, the lens used includes a lens that is transparent from the visible range to nIR and having a relatively high NA and resolution (e.g., using a lens having a magnification of at least 100×). In another implementation, one or more anti-reflective (AR) coatings are formed on one or more lens surface and is adapted to reduce loss of light passing through the lens due to reflections. In one specific application, the AR coating is adapted to reduce light reflection losses for light in a wavelength range of between about 700 and 1400 nanometers. In still another implementation, the lens used is adapted to use reflective optics, such as one employing an achromatic design.

The detector 240 may include one or more of a variety of high-speed optical detectors. For example, Schlumberger, Inc., of New York, N.Y. and Quantar Technology of Santa Cruz, Calif. (e.g., model 2601B MCP-PMT) manufacture detectors that can be used in connection with the present invention. In one implementation, the high-speed optical detector includes a detector adapted to detect light pulses having a duration of between about 0.1 and 50 picoseconds, such as a scanning optical microscope or a picosecond imaging circuit analysis (PICA) tool. In another implementation, the high-speed optical detector is adapted to detect light pulses having a duration exceeding about 50 picoseconds. For more information regarding the use of PICA and, more generally, to optical analysis, reference may be made to U.S. Patent application Ser. No. 09/409,974 (AMDA.314PA/TT3371), filed on Sep. 30, 1999 and entitled "Picosecond Imaging Circuit Analysis Probe and System," which is fully incorporated herein by reference. In various applications, the Zeiss 100×0.75 NA lens has been found advantageous for detecting photons from a SOI die having the insulator portion of the SOI structure exposed.

The power supply 260 is adaptable for a variety of implementations. For example, the die can be operated under normal conditions or under a known failure condition, and a response to the operation is detected. In another implementation, test data vectors are applied to the die via the power supply to operate the die under certain conditions, wherein the power supply includes a constant-voltage variable current source.

In a more particular implementation, a controller 250 is coupled to the photon detector 240 and to the power supply 260, and is adapted to receive a signal representing the photons detected at detector 240 and to effect the application of electrical signals to the die via the power supply. The signals detected using each of the two lenses are compared and the controller effects the use of the lens having the higher photon count to analyze the die.

Figure 3:
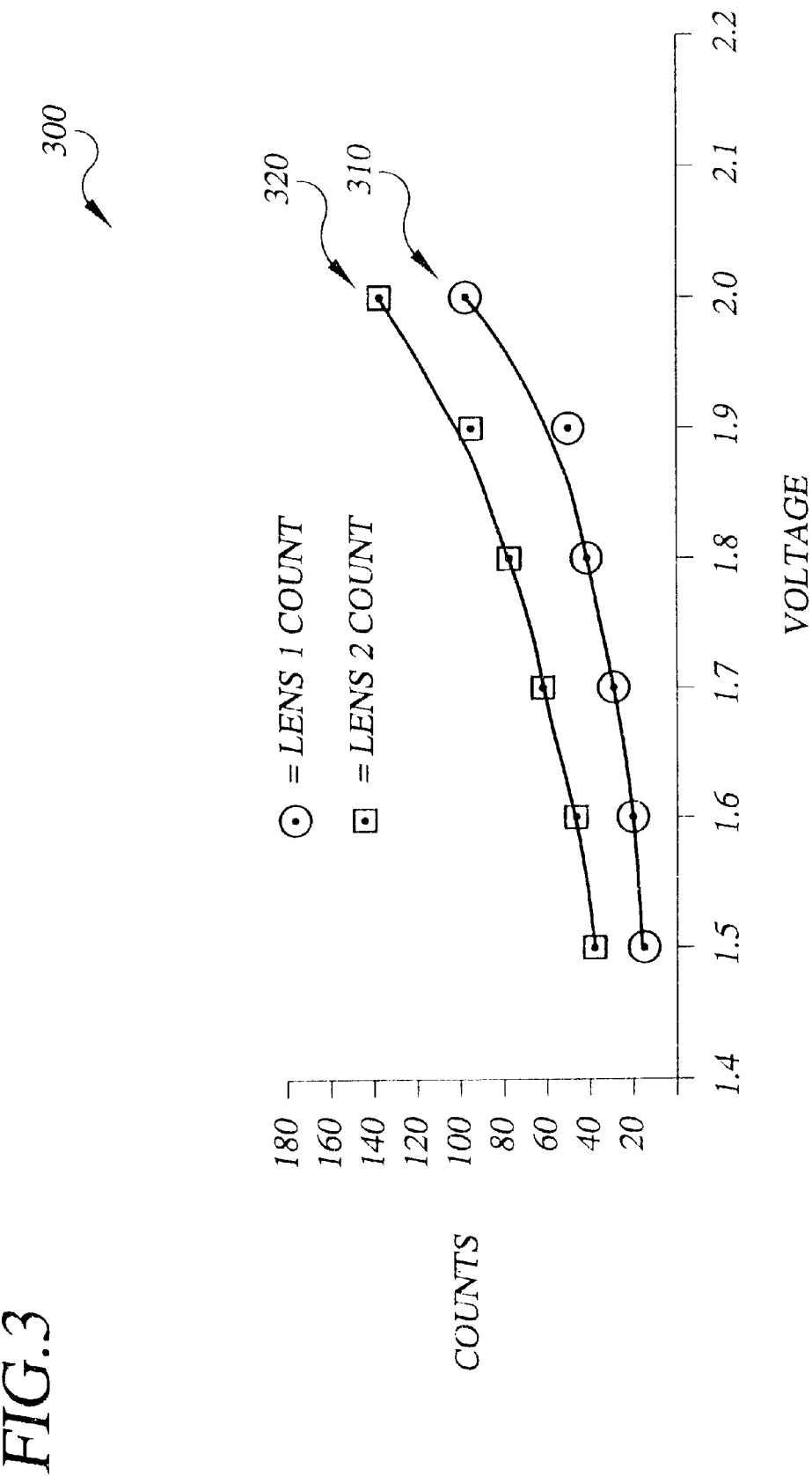
FIG. 3 is graph showing photon emission counts, used in connection with another example embodiment of the present invention.

FIG. 3 shows a graph 300 used to compare photon counts between two lenses, according to another example embodiment of the present invention. In one implementation, the graph 300 is displayed using the controller 250 of FIG. 2, and a user inputs a lens selection via the controller based on the graph. The graph shows detected photon counts at selected voltage levels, such as at a selected VDD voltage for a CMOS integrated circuit, with counts on the vertical axis and voltage level applied to the die on the horizontal axis. Curve 310 represents counts detected using a first lens, and curve 320 represents counts detected using a second lens. In this implementation, the second lens exhibits a higher photon count than the first lens, and is used to analyze the die.

While the present invention has been described with reference to several particular example embodiments, those skilled in the art will recognize that many changes may be made thereto without departing from the spirit and scope of the present invention, which is set forth in the following claims.

What is claimed is:

1. A method for analyzing an integrated circuit die having silicon on insulator (SOI) structure, the method comprising;
providing an integrated circuit die having at least a portion of the insulator of the SOI structure exposed;
stimulating the integrated circuit die;
detecting photon emissions including those in the visible region from the die via the SOI with a first lens in response to the stimulation;
detecting photon emissions including those in the visible region from the die via the SOI with a second lens that is different from the first lens in response to the stimulation;
comparing the photon emissions detected using the first and second lenses and identifying which of the first and second lenses has a higher photon count rate; and
using the lens having a higher photon count rate to detect photon emissions including those in the visible region from the die in response to the stimulation and analyzing the die therefrom.

2. The method of claim 1, wherein detecting photon emissions with the first lens includes using a lens having a plurality of lenses.

3. The method of claim 2, wherein using a lens having a plurality of lenses includes using a lens having two lenses and an interface between the lenses, the interface being arranged to eliminate an air to surface interface between the lenses.

4. The method of claim 1, wherein identifying which of the first and second lenses has a higher photon count rate includes identifying which lens has a higher photon count rate as a function of surface characteristics of the lens.

5. The method of claim 4, wherein identifying which lens has a higher photon count rate includes identifying the lens as a function of the numerical aperture (NA) and light loss due to reflected light.

6. The method of claim 1, wherein detecting photon emissions with the first lens includes using a lens having a NA of at least 0.7.

7. The method of claim 1, wherein detecting photon emissions with the first lens includes using a lens having an antireflective coating over at least one lens surface.

8. The method of claim 7, wherein using a lens having an antireflective coating includes using a lens having an antireflective coating that is adapted to reduce reflections of light having a wavelength of between about 700 and 1400 nanometers.

9. The method of claim 1, wherein detecting photon emissions with a first lens includes using a lens having reflective optics.

10. The method of claim 9, wherein using a lens having reflective optics includes using an achromatic lens.

11. The method of claim 1, wherein detecting photon emissions with the first lens includes directing a high-speed optical detector having the first lens at the die and wherein detecting photon emissions with the second lens includes directing a high-speed optical detector having the second lens at the die.

12. The method of claim 1, wherein identifying the lens having a higher photon count rate includes identifying the lens as a function of a characteristic of the exposed SOI structure.

13. The method of claim 1, further comprising using the lens having a higher photon count rate to detect photon emissions from a plurality of similarly manufactured dies having the SOI structure similarly exposed.

14. The method of claim 1, wherein analyzing the die includes detecting electron movement in the die.

15. The method of claim 14, wherein detecting electron movement includes detecting photon emissions caused by the electron movement.

16. The method of claim 1, wherein analyzing includes detecting a state-changing operation of a circuit device in the die.

17. The method of claim 1, further comprising using a third lens to obtain an image of the die and using the image for analyzing the die.

18. The method of claim 17, wherein using the image for analyzing the die includes using the image to survey a high-speed optical detector to a selected portion of the die, wherein using the lens having a higher photon count rate to detect a photon emission includes detecting the photon emission from the selected portion of the die.

19. The method of claim 18, further comprising using the third lens to survey to a second selected portion of the die and using the lens having the higher photon count rate to detect a photon emission from the second selected portion of the die.

20. The method of claim 17, wherein using the image for analyzing the die includes overlaying the image onto an image representing the detected photon emission and detecting a circuit element in the die that emitted the photon therefrom.

21. The method of claim 17, wherein using the lens having a higher photon count rate and using the third lens includes matching the magnification levels of the higher photon count lens and the third lens.

22. The method of claim 1, wherein stimulating the integrated circuit die includes using an integrated circuit test tool to provide test data vectors and thereby operate the die under normal conditions, and using a constant-voltage variable current source to power the die.

23. The method of claim 1, wherein stimulating the integrated circuit die includes operating the die to cause a known failure condition.

24. The method of claim 1, wherein detecting photon emissions from the die with the first and second lenses includes detecting light having a pulse length of between about one and five picoseconds.

25. The method of claim 1, further comprising correlating the time at which the light is detected to a stage in the operation of the die and identifying an operating state that the die is in at the stage in the operation of the die.

26. The method of claim 1, wherein using the lens having a higher photon count rate to detect a photon emission from the die includes obtaining an image of the photon emission, the image having a reference point, further comprising overlaying the image of the detected photon emission onto a circuit schematic using the reference point and detecting the source of the photon emission via the overlay.

27. The method of claim 1, wherein stimulating the integrated circuit die includes operating the die under similar conditions when detecting photon emissions using the first and second lenses.

28. The method of claim 1, wherein at least one of the first and second lenses include an immersion lens.

29. A system for analyzing an integrated circuit die having silicon on insulator (SOI) structure, the system comprising;
means for providing an integrated circuit die having at least a portion of the insulator of the SOI structure exposed;

means for stimulating the integrated circuit die;

means for detecting photon emissions including those in the visible region from the die via the SOI with a first lens in response to the stimulation;

means for detecting photon emissions including those in the visible region from the die via the SOI with a second lens that is different from the first lens in response to the stimulation;

means for comparing the photon emissions detected using the first and second lenses and identifying which of the first and second lenses has a higher photon count rate; and means for using the lens having a higher photon count rate to detect photon emissions including those in the visible region from the die in response to the stimulation and analyzing the die therefrom.

30. A system for analyzing an integrated circuit die having silicon on insulator (SOI) structure, the system comprising;

a substrate removal arrangement adapted to provide an integrated circuit die having at least a portion of the insulator of the SOI structure exposed;

a die analysis tool adapted to stimulate the integrated circuit die;

a detector adapted to detect photon emissions including those in the visible region from the die via the SOI with a first lens in response to the stimulation;

a detector adapted to detect photon emissions including those in the visible region from the die via the SOI with a second lens that is different from the first lens in response to the stimulation;

a comparison arrangement adapted to compare the photon emissions detected using the first and second lenses and to identify which of the first and second lenses has a higher photon count rate; and a detector adapted to use the lens having a higher photon count rate to detect photon emissions from the die in response to the stimulation for analyzing the die therefrom.

* * * * *

UNITED STATES PATENT AND TRADEMARK OFFICE
CERTIFICATE OF CORRECTION

PATENT NO. : 6,716,683 B1
DATED : April 6, 2004
INVENTOR(S) : Bruce et al.

It is certified that error appears in the above-identified patent and that said Letters Patent is hereby corrected as shown below:

<u>Title page,</u>
Item [73], Assignee, "Advanced Mircor Devices, Inc., Sunnyvale, CA (US)" should read -- Advanced Micro Devices, Inc., Sunnyvale, Ca (US) --

Signed and Sealed this

Twenty-second Day of June, 2004

JON W. DUDAS
*Acting Director of the United States Patent and Trademark Office*